(12) United States Patent
Kogo et al.

(10) Patent No.: US 8,193,338 B2
(45) Date of Patent: Jun. 5, 2012

(54) PROCESS FOR PRODUCING DI(PYRIMIDINE NUCLEOSIDE 5'-)POLYPHOSPHATE

(75) Inventors: Satoru Kogo, Choshi (JP); Kohei Yamada, Choshi (JP); Yuko Iwai, Koto-ku (JP); Kazuomi Osawa, Choshi (JP); Hiroyuki Hayakawa, Choshi (JP)

(73) Assignee: Yamasa Corporation, Choshi-shi (JP)

( * ) Notice: Subject to any disclaimer, the term of this patent is extended or adjusted under 35 U.S.C. 154(b) by 411 days.

(21) Appl. No.: 12/375,152

(22) PCT Filed: Jul. 25, 2007

(86) PCT No.: PCT/JP2007/000793
§ 371 (c)(1),
(2), (4) Date: Jan. 26, 2009

(87) PCT Pub. No.: WO2008/012949
PCT Pub. Date: Jan. 31, 2008

(65) Prior Publication Data
US 2010/0016567 A1    Jan. 21, 2010

(30) Foreign Application Priority Data
Jul. 26, 2006 (JP) .................. 2006-203124

(51) Int. Cl.
| C07H 21/00 | (2006.01) |
| C07H 19/00 | (2006.01) |
| C07H 19/048 | (2006.01) |
| C07H 19/06 | (2006.01) |
| C07H 19/04 | (2006.01) |
| C07H 21/02 | (2006.01) |
| C07H 21/04 | (2006.01) |
| C07H 1/00 | (2006.01) |
| C07H 3/00 | (2006.01) |
| C08B 37/00 | (2006.01) |
| A01N 43/04 | (2006.01) |
| A61K 31/70 | (2006.01) |

(52) U.S. Cl. ............ 536/25.6; 536/28.1; 536/28.4; 536/124; 536/26.1; 536/23.1; 514/49; 514/51

(58) Field of Classification Search .............. 536/25.6, 536/28.1, 28.4, 124, 26.1, 23.1; 514/49, 514/51
See application file for complete search history.

(56) References Cited

U.S. PATENT DOCUMENTS
5,837,861 A    11/1998   Pendergast et al.
6,348,589 B1 *  2/2002   Pendergast et al. ......... 536/25.6

FOREIGN PATENT DOCUMENTS
JP    2001 526635    12/2001
WO   WO 99/05155    2/1999

OTHER PUBLICATIONS

Shimazu, M., Shinozuka, K., Sawai, H. (1990) Facile Synthesis of Nucleotides Containing Polyphosphates by Mn(II) and Cd(II) Ion-Catalyzed Pyrophosphate Bond Formation in Aqueous Solution. Tetrahedron Letters, vol. 31, No. 2, p. 235-238.*

Pendergast, William et al., "Synthesis and P2Y Receptor Activity of a Series of Uridine Dinucleoside 5'-Polyphosphates", Bioorganic & Medicinal Chemistry Letters, vol. 11, No. 2, pp. 157-160, (2001).

Han, Qianwei et al., "One-Flask Synthesis of Dinucleoside Tetra- and Pentaphosphates", Organic Letters, vol. 8, No. 10, pp. 2075-2077, (2006).

Office Action issued Apr. 25, 2011, in Chinese Patent Application No. 200780028646.9 (with partial English translation).

Kobayashi, Shu, et al. Accounts of Chemical Research, vol. 35, No. 4. "Development of Novel Lewis Acid Catalysts for Selective Organic Reactions in Aqueous Media". 2002. pp. 209-217.

Kadokura, Michinori, et al. Tetrahedron Letters, vol. 38, No. 48. "Efficient Synthesis of γ-Methyl-Capped Guanosine 5'-Triphosphate as a 5'-Terminal Unique Structure of a U6 RNA via a New Triphosphate Bond Formation Involving Activation of Methyl Phosphorimidazolidate Using ZnCl2 as a Catalyst in DMF under Anhydrous Conditions". 1997. pp. 8359-8362.

Sawai, H., et al. Nucleosides and Nucleotides. vol. 11, (2-4). "Divalent Metal Ion-Catalyzed Pyrophosphate Bond Formation in Aqueous Solution-Synthesis of Nucelotides Containing Polyphosphate". 1992. pp. 773-785.

* cited by examiner

Primary Examiner — Scarlett Goon
(74) Attorney, Agent, or Firm — Oblon, Spivak, McClelland, Maier & Neustadt, L.L.P.

(57) ABSTRACT

A di(pyrimidine nucleoside 5'-)polyphosphate is synthesized by converting a pyrimidine nucleoside 5'-triphosphate into a pyrimidine nucleoside 5'-cyclic triphosphate by use of a condensing agent, and subsequently reacting the pyrimidine nucleoside 5'-cyclic triphosphate with a pyrimidine nucleotide in the presence of a salt of a metal selected from among magnesium, manganese, and iron.

Through the method of the invention, a di(pyrimidine nucleoside 5'-)polyphosphate can be synthesized from an unprotected pyrimidine nucleoside 5'-phosphate serving as a starting material at a synthesis yield of 50% or higher. Therefore, the method of the invention is suitable for large-scale synthesis of a di(pyrimidine nucleoside 5'-)polyphosphate.

16 Claims, No Drawings

PROCESS FOR PRODUCING DI(PYRIMIDINE NUCLEOSIDE 5'-)POLYPHOSPHATE

TECHNICAL FIELD

The present invention relates to a method for effectively producing di(pyrimidine nucleoside 5'-)polyphosphate.

BACKGROUND ART

Among di(pyrimidine nucleoside 5'-)polyphosphates represented by the following formula (I):

[F1]

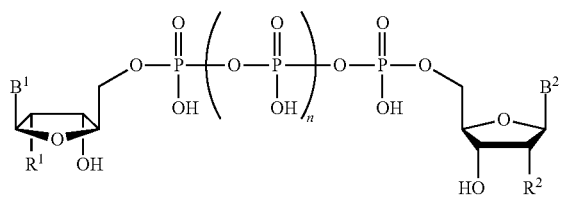

(I)

(wherein, each of $R^1$ and $R^2$, which may be identical to or different from each other, represents a hydrogen atom or a hydroxyl group; each of $B^1$ and $B^2$, which may be identical to or different from each other, represents a pyrimidine base; and n is an integer from 1 to 4), for example, $P^1,P^4$-di(uridine 5'-)tetraphosphate (Up4U) or a salt thereof is a compound which exhibits an expectoration-inducing effect and thus is envisaged to be developed as an expectorant or a therapeutic drug for pneumonia, and $P^1$-(2'-deoxycytidine 5'-)$P^4$-(uridine 5'-)tetraphosphate (dCp4U) or a salt thereof is a compound which is a selective agonist for P2Y2 and/or P2Y4 purine receptor and thus is envisaged to be developed as a therapeutic drug for, for example, chronic bronchitis or sinusitis.

In a method for synthesizing such a di(pyrimidine nucleoside 5'-)polyphosphate, for example, Up4U is produced from uridine 5'-monophosphate (UMP) serving as a starting material by use of an activator (e.g., diphenyl phosphorochloridate (DPC)) and a phosphorylating agent (e.g., pyrophosphate (PPi)). However, such a method has failed to be put into practice, since the method produces a target compound at a very low synthesis yield (i.e., a little less than 10% or thereabouts) (Patent Document 1).

For improvement of such a method, attempts have been made to develop a method for synthesizing a di(pyrimidine nucleoside 5'-)polyphosphate via a nucleoside 5'-cyclic triphosphate. Specifically, there have been reported a method for preparing Up4U by reacting uridine 5'-cyclic triphosphate with UMP (Non-Patent Document 1), and a method for preparing $P^1,P^4$-di(adenosine 5'-)tetraphosphate by reacting adenosine 5'-cyclic triphosphate with adenosine 5'-monophosphate (Non-Patent Document 2).
Patent Document 1: WO99/5155
Non-Patent Document 1: Bioorganic & Medicinal Chemistry Letters, 11 (2001), 157-160
Non-Patent Document 2: Organic Letters, Vol. 8, No. 10, 2075-2077 (2006)

DISCLOSURE OF THE INVENTION

Problems to be Solved by the Invention

As has been reported, Up4U can be synthesized at a yield of 32% through the aforementioned method for preparing Up4U by reacting uridine 5'-cyclic triphosphate with UMP (Non-Patent Document 1). However, this method requires a high reaction temperature (i.e., 40° C.) and thus poses problems in that purifying the target product is very difficult, since large amounts of by-products (other than the target product) are produced under heating at such a temperature. Particularly when an asymmetric di(pyrimidine nucleoside 5'-)polyphosphate (e.g., dCp4U) is synthesized under heating, symmetric Up4U, which has a structure very similar to that of the target product, is by-produced, and, regardless of the various purification conditions, it is almost impossible to separate the by-product from the target product. This indicates that reaction between a nucleoside 5'-cyclic triphosphate and a nucleoside 5'-monophosphate at a temperature around room temperature is important for preventing an increase in amount of by-products. However, when such a reaction was carried out at a temperature around room temperature, as described in detail in the Examples hereinbelow, the aforementioned yield failed to be attained, and Up4U was synthesized at a very low yield (i.e., 10% or less).

Meanwhile, the non-patent document which reports the method for preparing $P^1,P^4$-di(adenosine 5'-)tetraphosphate by reacting adenosine 5'-cyclic triphosphate with adenosine 5'-monophosphate suggests that this method is applicable to various di(nucleoside 5'-)polyphosphates. However, the document shows no specific data which would be obtained from application of the method to synthesis of a di(pyrimidine nucleoside 5'-)polyphosphate. The method employs, as a raw material compound, a nucleotide having protected hydroxyl and amino groups, and thus requires deprotection of the protected groups after synthesis of a target compound, which requires an intricate process and reduces the yield. In addition, the method is disadvantageous in terms of cost, since the method requires excessive amounts of reagents used for reaction. More importantly, when the present inventors conducted a follow-up test by applying the method to synthesis of a di(pyrimidine nucleoside 5'-)polyphosphate, the target compound was synthesized at a low yield; i.e., the method is never satisfactory, as described in the Examples hereinbelow.

Means for Solving the Problems

In order to solve the aforementioned problems, the present inventors have conducted extensive studies, and as a result have found that when a pyrimidine nucleoside 5'-cyclic triphosphate is reacted with a pyrimidine nucleotide in the presence of a specific metal salt (in particular, a magnesium salt), even at room temperature, a target di(pyrimidine nucleoside 5'-)polyphosphate can be synthesized at a yield considerably higher than that attained by the aforementioned known methods. The present invention has been accomplished on the basis of this finding. Accordingly, the present invention provides the following.

[1] A method for producing a di(pyrimidine nucleoside 5'-)polyphosphate, comprising converting a pyrimidine nucleoside 5'-triphosphate into a pyrimidine nucleoside 5'-cyclic triphosphate by use of a condensing agent, and subsequently reacting the pyrimidine nucleoside 5'-cyclic triphosphate with a pyrimidine nucleotide in the presence of a salt of a metal selected from among magnesium, manganese, and iron.

[2] A production method according to [1] above, wherein the di(pyrimidine nucleoside 5'-)polyphosphate is a compound represented by the following formula (I):

[F2]

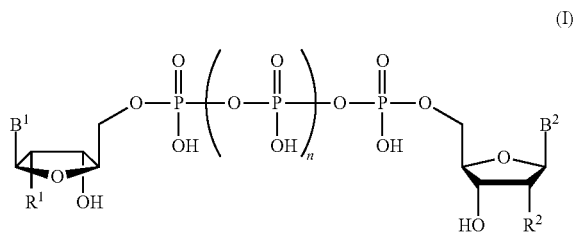

(I)

(wherein each of $R^1$ and $R^2$, which may be identical to or different from each other, represents a hydrogen atom or a hydroxyl group; each of $B^1$ and $B^2$, which may be identical to or different from each other, represents a pyrimidine base; and n is an integer from 1 to 4).

[3] A production method according to [1] above, wherein the condensing agent is a carbodiimide.

[4] A production method according to [1] above, wherein the metal salt is a magnesium salt.

[5] A production method according to [1] above, wherein reaction is carried out at 15 to 30° C.

[6] A production method according to [1] above, wherein $P^1,P^4$-di(uridine 5'-)tetraphosphate (Up4U) is produced from uridine 5'-triphosphate (UTP) and uridine 5'-monophosphate (UMP).

[7] A production method according to [1] above, wherein $P^1,P^5$-di(uridine 5'-)pentaphosphate (Up5U) is produced from uridine 5'-triphosphate (UTP) and uridine 5'-diphosphate (UDP).

[8] A production method according to [1] above, wherein $P^1$-(2'-deoxycytidine 5'-)$P^4$-(uridine 5'-)tetraphosphate (dCp4U) is produced from uridine 5'-triphosphate (UTP) and 2'-deoxycytidine 5'-monophosphate (dCMP).

[9] A production method according to [1] above, wherein $P^1$-(2'-deoxycytidine 5'-)$P^4$-(uridine 5'-)tetraphosphate (dCp4U) is produced from 2'-deoxycytidine 5'-triphosphate (dCTP) and uridine 5'-monophosphate (UMP).

Effects of the Invention

The most distinguishing feature of the synthesis method of the present invention resides in that a pyrimidine nucleoside 5'-triphosphate is converted into a pyrimidine nucleoside 5'-cyclic triphosphate, and subsequently the pyrimidine nucleoside 5'-cyclic triphosphate is reacted with a pyrimidine nucleotide in the presence of a salt of a metal selected from among magnesium, manganese, and iron (in particular, a magnesium salt).

According to the aforementioned conventional methods, a pyrimidine nucleoside 5'-cyclic triphosphate is reacted with a pyrimidine nucleotide in the absence of a metal salt (Non-Patent Document 1) or in the presence of a zinc salt (Non-Patent Document 2).

However, studies by the present inventors have shown that the method described in Non-Patent Document 1 (i.e., the method for synthesizing a di(pyrimidine nucleoside 5'-)polyphosphate via a nucleoside 5'-cyclic triphosphate in the absence of a metal salt) produces a di(pyrimidine nucleoside 5'-)polyphosphate at a very low synthesis yield. In addition, the synthesis method requires a relatively high reaction temperature (i.e., 40° C.) and thus produces large amounts of by-products other than the target product, which causes great difficulty in purifying the target product.

Meanwhile, the method described in Non-Patent Document 2 (i.e., the method in which a nucleoside 5'-cyclic triphosphate is reacted with a nucleotide in the presence of a zinc salt) is suitable for synthesis of $P^1,P^4$-di(adenosine 5'-)tetraphosphate. However, studies by the present inventors have shown that this method does not necessarily produce a di(pyrimidine nucleoside 5'-)polyphosphate at a high synthesis yield; i.e., the method is not suitable for synthesis of a di(pyrimidine nucleoside 5'-)polyphosphate.

Under such circumstances, the present inventors have first indicated that, quite unexpectedly, a magnesium salt, which in Non-Patent Document 2 is shown to be less effective than a zinc salt, is very effective for synthesis of a di(pyrimidine nucleoside 5'-)polyphosphate. According to the method of the present invention, a target compound can be synthesized from an unprotected nucleotide compound serving as a starting material through a simple process requiring no protection-deprotection process at a synthesis yield of 50.5 to 94.3%, which is considerably higher than that attained by the conventional methods. In addition, the method of the present invention is advantageous in that, since reaction is carried out under mild conditions (i.e., a reaction temperature around room temperature), by-products are produced in small amounts, and the target compound is readily purified. Therefore, the method of the present invention is suitable for synthesis of a di(pyrimidine nucleoside 5'-)polyphosphate in a large amount on an industrial scale.

BEST MODES FOR CARRYING OUT THE INVENTION

As described above, in the method of the present invention, a pyrimidine nucleoside 5'-triphosphate is converted into a pyrimidine nucleoside 5'-cyclic triphosphate by use of a condensing agent, and subsequently the pyrimidine nucleoside 5'-cyclic triphosphate is reacted with a pyrimidine nucleotide in the presence of a salt of a metal selected from among magnesium, manganese, and iron, to thereby synthesize a di(pyrimidine nucleoside 5'-)polyphosphate.

The condensing agent employed for converting a pyrimidine nucleoside 5'-triphosphate into a pyrimidine nucleoside 5'-cyclic triphosphate may be a known condensing agent, such as a carbodiimide (e.g., dicyclohexylcarbodiimide (DCC), water-soluble carbodiimide (WSC), or diisopropylcarbodiimide (DIPC)), carbonyldiimidazole (CDI), a phosphate halide (e.g., diphenyl phosphorochloridate (DPC)), or a sulfonic acid halide (e.g., toluenesulfonyl chloride). Particularly, a carbodiimide is preferably employed.

Reaction conditions may vary with the type of a condensing agent employed. For example, conversion may be carried out by reacting a condensing agent (1 to 5 mol) with 1 mol of a pyrimidine nucleoside 5'-triphosphate (NTP) in a single solvent (e.g., dimethylformamide (DMF), dimethylacetamide (DMA), formamide (FA), pyridine, dioxane, or dimethyl sulfoxide) or a mixture thereof at 0° C. to 50° C. (preferably 15 to 30° C.) for about 1 to about 10 hours.

More specifically, in the case where DIPC is employed as a condensing agent, conversion may be carried out by reacting DIPC (1 to 5 mol, preferably 1.2 to 1.4 mol) with 1 mol of NTP in DMF at 0° C. to 50° C. (preferably 20 to 30° C.) for about 3 to about 5 hours.

Subsequently, the thus-obtained pyrimidine nucleoside 5'-cyclic triphosphate is reacted, without being isolated, with a pyrimidine nucleotide in the presence of a salt of a metal selected from among magnesium, manganese, and iron, to thereby synthesize a di(pyrimidine nucleoside 5'-)polyphosphate.

No particular limitation is imposed on the metal salt employed for reaction, so long as it is a salt of a metal selected from among magnesium, manganese, and iron. Specific examples of the metal salt include metal halides such as magnesium fluoride, magnesium chloride, magnesium bromide, magnesium iodide, manganese chloride, and ferric chloride; inorganic acid salts of metals, such as sulfates, nitrates, phosphates, perchlorates, and tetrafluoroborates of magnesium, manganese, and iron; and organic acid salts of metals, such as trifluoromethanesulfonates, methanesulfonates, toluenesulfonates, acetates, trifluoroacetates, stearates, and citrates of magnesium, manganese, and iron.

Among these metal salts, a magnesium salt (in particular, magnesium chloride) is preferred, from the viewpoints of synthesis yield and easy handling. The metal salt employed may be in the form of anhydrate or hydrate.

Synthesis may be carried out by adding a pyrimidine nucleotide (1 to 5 mol, preferably 1.0 to 1.3 mol) and a metal salt (1 to 5 mol, preferably 1.0 to 1.3 mol) to 1 mol of the above-obtained pyrimidine nucleoside 5'-cyclic triphosphate, followed by reaction at 0 to 1000° C. (preferably 15 to 30° C.) for about 1 to about 24 hours.

After completion of reaction, the thus-synthesized di(pyrimidine nucleoside 5'-)polyphosphate (i.e., target product) may be isolated and purified through appropriate combination of generally used nucleotide isolation/purification techniques (e.g., recrystallization, ion-exchange column chromatography, adsorption column chromatography, and activated carbon column chromatography). If necessary, the di(pyrimidine nucleoside 5'-)polyphosphate may be provided in the form of salt.

Examples of the ion-exchange resin which may be employed in ion-exchange column chromatography include basic anion-exchange resins (e.g., Amberlite IRA 402 [product of Rohm & Haas], and Diaion PA-312 and Diaion SA-11A [products of Mitsubishi Chemical Corporation]), weakly basic anion-exchange resins (e.g., Amberlite IRA 67 [product of Rohm & Haas] and Diaion WA-30 [product of Mitsubishi Chemical Corporation]), strongly acidic cationic-exchange resins (e.g., Diaion PK-216 [product of Mitsubishi Chemical Corporation]), and weakly acidic cation-exchange resins (e.g., Diaion WK-30 [product of Mitsubishi Chemical Corporation]).

The activated carbon employed may be ground or granulated activated carbon for chromatography; for example, activated carbon commercially available from Wako Pure Chemical Industries, Ltd. or Futamura Chemical Co., Ltd.

Recrystallization is carried out by adding a hydrophilic organic solvent to the thus-purified di(pyrimidine nucleoside 5'-)polyphosphate or a salt thereof for precipitation of crystals. Examples of the hydrophilic organic solvent employed include alcohols having six or less carbon atoms, such as methanol and ethanol; ketones such as acetone; ethers such as dioxane; nitriles such as acetonitrile; and amides such as dimethylformamide. Particularly, alcohols (preferably ethanol) are employed.

The above-described method of the present invention is applicable to production of a di(pyrimidine nucleoside 5'-)polyphosphate; specifically, for example, a di(pyrimidine nucleoside 5'-)polyphosphate represented by formula (I), and the method is not limited to production of a specific compound. The method of the present invention is applicable to, for example, (1) synthesis of $P^1,P^4$-di(uridine 5'-)tetraphosphate (Up4U) from uridine 5'-triphosphate (UTP) and uridine 5'-monophosphate (UMP), (2) synthesis of $P^1,P^5$-di(uridine 5'-)pentaphosphate (Up5U) from uridine 5'-triphosphate (UTP) and uridine 5'-diphosphate (UDP), (3) synthesis of $P^1$-(2'-deoxycytidine 5'-)$P^4$-(uridine 5'-)tetraphosphate (dCp4U) from uridine 5'-triphosphate (UTP) and 2'-deoxycytidine 5'-monophosphate (dCMP), or (4) synthesis of $P^1$-(2'-deoxycytidine 5'-)$P^4$-(uridine 5'-)tetraphosphate (dCp4U) from 2'-deoxycytidine 5'-triphosphate (dCTP) and uridine 5'-monophosphate (UMP).

EXAMPLES

The present invention will next be described in detail by way of examples, which should not be construed as limiting the invention thereto.

Example 1

Effect of Metal Salt on Synthesis Yield of $P^1,P^4$-di(uridine 5'-)tetraphosphate (Up4U)

(1) Preparation of Dimethylformamide Solution of Uridine 5'-cyclic Triphosphate (cUTP)

Uridine 5'-triphosphate (UTP) trisodium salt (5.00 g, 9.10 mmol) was dissolved in deionized water to yield 50 mL of a solution, and the solution was caused to pass through a strong cation-exchange column (PK 216, proton-type, 27 cc). The eluate was mixed with a column wash solution, and the mixture was neutralized with tributylamine (8.7 mL, 37 mmol). The resultant solution was concentrated under reduced pressure, and the residue was co-boiled four times with dioxane (20 mL). The residue was dissolved in dimethylformamide (50 mL), to thereby yield a 0.15 M dimethylformamide solution of UTP tributylamine salt. Diisopropylcarbodiimide (1,535 µL, 10.0 mmol) was added to the dimethylformamide solution, followed by stirring at room temperature for three hours, to thereby prepare a 0.15 M dimethylformamide solution of cUTP tributylamine salt.

(2) Preparation of Dimethylformamide Solution of Uridine 5'-monophosphate (UMP) Tributylamine Salt Tributylamine (4.4 mL, 19 mmol) was added to a 2.05 M aqueous UMP solution (4.4 mL, 9.0 mmol), and the mixture was concentrated. The residue was co-boiled six times with dioxane (20 mL) and then dissolved in dimethylformamide (50 mL), to thereby prepare a 0.18 M dimethylformamide solution of UMP tributylamine salt.

(3) Evaluation of Effect of Metal Salt on Reaction Between cUTP and UMP

The 0.18 M dimethylformamide solution of UMP tributylamine salt prepared above in (2) (500 µL, 90.0 µmol) and a 0.45 M dimethylformamide solution of a metal salt shown in Table 1 (200 µL, 90.0 µmol) were added to the 0.15 M dimethylformamide solution of cUTP tributylamine salt prepared above in (1) (500 µL, 75.0 µmol), followed by reaction at room temperature (25° C.) for one hour. The reaction mixture was analyzed through HPLC (262 nm), and the synthesis yield of Up4U (i.e., target product) was determined. The results are shown in Table 1.

TABLE 1

| Entry | Metal salt (1.2 equivalents) | cUTP (equivalent) | UMP (equivalent) | Up4U Synthesis yield (%) |
|---|---|---|---|---|
| 1 | Anhydrous $MgCl_2$ | 1 | 1.2 | 80.2% |
| 2 | $MgCl_2$—$6H_2O$ | | | 84.0% |

TABLE 1-continued

| Entry | Metal salt (1.2 equivalents) | cUTP (equivalent) | UMP (equivalent) | Up4U Synthesis yield (%) |
|---|---|---|---|---|
| 3 | Mg(OTf)$_2$ | | | 67.9% |
| 4 | MnCl$_2$—4H$_2$O | | | 72.2% |
| 5 | FeCl$_3$ | | | 64.9% |
| 6 | Zn(OTf)$_2$ | | | 24.7% |
| 7 | ZnCl$_2$ | | | 19.1% |
| 8 | — | | | 3.8% |

OTf: Trifluoromethanesulfonate

As shown in Table 1, when Up4U was synthesized from cUTP and UMP in the absence of a metal salt, the synthesis yield of Up4U was 3.8% (entry 8, the method described in Non-Patent Document 1), whereas when Up4U was synthesized from cUTP and UMP in the presence of a zinc salt, the synthesis yield of Up4U was 19.1 to 24.7% (entries 6 and 7, the method described in Non-Patent Document 2). In contrast, when Up4U was synthesized from cUTP and UMP in the presence of a salt of a metal selected from among iron, manganese, and magnesium, the synthesis yield of Up4U considerably increased to 60% or more (particularly in the presence of a magnesium salt, a synthesis yield of 80% or more was achieved) (entries 1 to 5).

Example 2

Synthesis of Up4U Sodium Salt (1) Dimethylformamide Solution of UTP Tributylamine Salt
UTP trisodium salt (1.00 g, 1.82 mmol) was dissolved in deionized water (13 mL), and the solution was caused to pass through a strong cation-exchange column (PK 216, proton-type, 10 cc). The eluate was mixed with a column wash solution, and the mixture was neutralized with tributylamine (1.75 mL, 7.35 mmol). The resultant solution was concentrated under reduced pressure, and the residue was co-boiled four times with dioxane (10 mL). The residue was dissolved in dimethylformamide (10 mL), to thereby yield a 0.133 M dimethylformamide solution of UTP tributylamine salt.

(2) Dimethylformamide Solution of UMP Tributylamine Salt
Tributylamine (1.06 mL, 4.46 mmol) was added to a 2.05 M aqueous UMP solution (1.06 mL, 2.18 mmol), and the mixture was concentrated. The residue was co-boiled four times with dioxane (10 mL) and then dissolved in dimethylformamide (10 mL), to thereby prepare a 0.184 M dimethylformamide solution of UMP tributylamine salt.

(3) Synthesis of Up4U
Diisopropylcarbodiimide (364 µL, 2.37 mmol) was added to the dimethylformamide solution of UTP tributylamine salt prepared above in (1), and the mixture was stirred at room temperature for three hours. To the mixture were added the 0.184 M dimethylformamide solution of UMP tributylamine salt prepared above in (2) and a solution of anhydrous magnesium chloride (207.5 mg, 2.179 mmol) in dimethylformamide (4.9 mL), followed by stirring at room temperature for 255 minutes. The resultant reaction mixture was analyzed through HPLC (262 nm). As a result, Up4U (i.e., target product) was found to be produced from UTP at a synthesis yield of 84.2%.

(4) Purification and Isolation of Up4U
Deionized water (6.5 mL) was added to the reaction mixture obtained above in (3), and the mixture was concentrated under reduced pressure. Deionized water (25 mL) was added to the residue, and the resultant precipitate was removed through filtration and washed with deionized water. Subsequently, the filtrate was mixed with the precipitate wash solution, and the mixture was caused to pass through a strong cation-exchange column (PK 216, proton-type, 20 cc). The eluate was mixed with a column wash solution, and the pH of the mixture was adjusted to 7.5 with triethylamine. The resultant solution was adsorbed on an anion-exchange column (IRA 67, chloride-ion-type, 40 cc), and the column was washed sequentially with 0.15 N hydrochloric acid and deionized water. Thereafter, the target product was eluted with a 0.3 to 0.4 M aqueous ammonium hydrogencarbonate solution. A fraction containing the target product was concentrated under reduced pressure, and then the residue was co-boiled with deionized water, followed by lyophilization. The resultant residue was dissolved in deionized water, and then the solution was caused to pass through a strong cation-exchange column (PK 216, sodium-type, 40 cc). The eluate was mixed with a column wash solution, and the mixture was concentrated under reduced pressure. The residue was dissolved in deionized water, and ethanol was added to the solution, followed by cooling. The thus-precipitated crystals were filtered, to thereby yield Up4U sodium salt (1.08 g, 1.23 mmol, 67.7%).

Example 3

Synthesis of $P^1,P^5$-di(uridine 5'-)pentaphosphate (Up5U)

A 0.154 M dimethylformamide solution of uridine 5'-diphosphate (UDP) tributylamine salt (584 µL, 90.0 µmol) and a 0.45 M dimethylformamide solution of anhydrous magnesium chloride (200 µL, 90.0 µmol) were added to a 0.15 M dimethylformamide solution of cUTP tributylamine salt (500 µL, 75.0 µmol), and the mixture was stirred at room temperature for 72 hours. The resultant reaction mixture was analyzed through HPLC (262 nm). As a result, Up5U (i.e., target product) was found to be produced from UTP at a synthesis yield of 50.5%.

Example 4

Synthesis of $P^1$-(2'-deoxycytidine 5'-)$P^4$-(uridine 5'-)tetraphosphate (dCp4U) from 2'-deoxycytidine 5'-triphosphate (dCTP) Serving as a Starting Material Diisopropylcarbodiimide (3.4 µL, 22.1 µmol) was added to a 0.144 M dimethylformamide solution of dCTP tributylamine salt (166 µL, 16.7 µmol), and the mixture was stirred at room temperature for three hours. To the mixture were added a 0.18 M dimethylformamide solution of UMP tributylamine salt and a 0.45 M dimethylformamide solution of anhydrous magnesium chloride or zinc chloride so that the equivalents of UMP and the metal salt were as shown in Table 2, followed by stirring at room temperature for one hour. The resultant reaction mixture was analyzed through HPLC (272 nm), and the synthesis yield of dCp4U (i.e., target product) was determined. The results are shown in Table 2.

TABLE 2

| Entry | dCTP (equivalent) | UMP (equivalent) | Metal salt (equivalent) | dCp4U Synthesis yield (%) |
|---|---|---|---|---|
| 1 | 1 | 1.2 | Anhydrous MgCl$_2$ 1.2 | 66.0% |
| 2 | | 2.4 | Anhydrous MgCl$_2$ 2.4 | 77.2% |

TABLE 2-continued

| Entry | dCTP (equivalent) | UMP (equivalent) | Metal salt (equivalent) | dCp4U Synthesis yield (%) |
|---|---|---|---|---|
| 3 | | 3.4 | Anhydrous MgCl$_2$ 9.36 | 81.0% |
| 4 | | 1.2 | ZnCl$_2$ 1.2 | 9.58% |
| 5 | | 3.4 | ZnCl$_2$ 9.36 | 35.0% |

As shown in Table 2, when UMP (1.2 to 2.4 equivalents) was reacted with 1 equivalent of dCTP in the presence of magnesium chloride (1.2 to 2.4 equivalents) for one hour, dCp4U was produced from dCTP at a high synthesis yield of 66.0 to 77.2%. In contrast, reaction in the presence of zinc chloride produced the target compound at only a low synthesis yield of 10% or less, and increasing the amount (equivalent) of zinc chloride did not lead to a considerable increase in yield of the target compound.

Example 5

Synthesis of $P^1$-(2'-deoxycytidine 5'-)$P^4$-(uridine 5'-)tetraphosphate (dCp4U) from uridine 5'-triphosphate (UTP) Serving as a Starting Material A 0.15 M dimethylformamide solution of cUTP tributylamine salt, a 0.15 M formamide solution of 2'-deoxycytidine 5'-monophosphate (dCMP) tributylamine salt, and a 0.45 M dimethylformamide solution of magnesium chloride hexahydrate were mixed in proportions shown in Table 3, and dimethylformamide was added to the mixture so that the total amount of the resultant mixture was 1 mL. The mixture was stirred at room temperature for one hour, and then the resultant reaction mixture was analyzed through HPLC (272 nm), to thereby determine the synthesis yield of dCp4U (i.e., target product).

TABLE 3

| Entry | 0.15 M cUTP (equivalent) | 0.15 M dCMP (equivalent) | 0.45 M MgCl$_2$ 6H$_2$O (equivalent) | dCp4U Synthesis yield (%)* |
|---|---|---|---|---|
| 1 | 200 µL (1) | 200 µL (1) | 67 µL (1) | 51.7% |
| 2 | 200 µL (1) | 240 µL (1.2) | 67 µL (1) | 54.7% |
| 3 | 300 µL (1.5) | 200 µL (1) | 100 µL (1.5) | 65.9% |
| 4 | 400 µL (2) | 200 µL (1) | 133 µL (2) | 94.3% |
| 5 | 500 µL (2.5) | 200 µL (1) | 167 µL (2.5) | 91.3% |
| 6 | 200 µL (1) | 200 µL (1) | — | 14.0% |

*Synthesis yield of dCp4U from dCMP

As is clear from Table 3, when dCMP is reacted with cUTP in the presence of magnesium chloride for one hour, dCp4U is virtually stoichiometrically produced from dCMP. As is also clear from Table 3, the yield of dCp4U is considerably reduced in the absence of magnesium chloride.

The invention claimed is:

1. A method for producing a di(pyrimidine nucleoside 5'-)polyphosphate, comprising converting a pyrimidine nucleoside 5'-triphosphate into a pyrimidine nucleoside 5'-cyclic triphosphate by use of a condensing agent, and subsequently reacting the pyrimidine nucleoside 5'-cyclic triphosphate with a pyrimidine nucleotide in the presence of a salt of a metal selected from the group consisting of magnesium, manganese, and iron, in a single solvent selected from the group consisting of dimethylformamide, dimethylacetamide, formamide, pyridine, dioxane, and dimethyl sulfoxide, or a mixture thereof.

2. A production method according to claim 1, wherein the metal salt is a magnesium salt.

3. A production method according to claim 1, wherein the di(pyrimidine nucleoside 5'-)polyphosphate is a compound represented by the following formula (I):

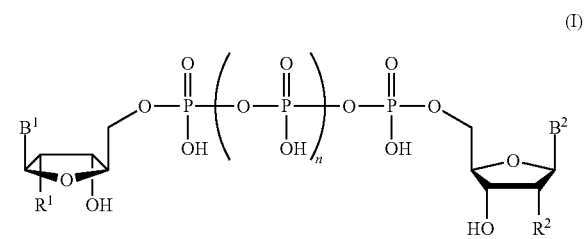

wherein each of $R^1$ and $R^2$, which may be identical to or different from each other, represents a hydrogen atom or a hydroxyl group; each of $B^1$ and $B^2$, which may be identical to or different from each other, represents a pyrimidine base; and n is an integer from 2 to 4.

4. A production method according to claim 1, wherein $P^1,P^4$-di(uridine 5'-)tetraphosphate is produced from uridine 5'-triphosphate and uridine 5'-monophosphate.

5. A production method according to claim 1, wherein $P^1,P^5$-di(uridine 5'-)pentaphosphate is produced from uridine 5'-triphosphate and uridine 5'-diphosphate.

6. A production method according to claim 1, wherein $P^1$-(2'-deoxycytidine 5'-)$P^4$-(uridine 5'-)tetraphosphate is produced from uridine 5'-triphosphate and 2'-deoxycytidine 5'-monophosphate.

7. A production method according to claim 1, wherein $P^1$-(2'-deoxycytidine 5'-)$P^4$-(uridine 5'-)tetraphosphate is produced from 2'-deoxycytidine 5'-triphosphate and uridine 5'-monophosphate.

8. A production method according to claim 1, wherein the reaction is carried out at 15 to 30° C.

9. A production method according to claim 1, wherein said reacting is at a temperature ranging from 0° C. to 50° C. for about 1 to about 10 hours.

10. A production method according to claim 1, wherein said reacting is at a temperature ranging from 15° C. to 30° C. for about 1 to about 10 hours.

11. A production method according to claim 1, wherein the condensing agent is a carbodiimide.

12. A production method according to claim 1, wherein the condensing agent is a diisopropylcarbodiimide.

13. A production method according to claim 12, wherein said reacting comprises mixing diisopropylcarbodiimide with pyrimidine nucleoside 5'-triphosphate at a relationship of 1 mol of pyrimidine nucleoside 5'-triphosphate per 1 to 5 mol of diisopropylcarbodiimide.

14. A production method according to claim 13, wherein said reacting is in dimethylformamide.

15. A production method according to claim 13, wherein said reacting is at a temperature ranging from 0° C. to 50° C. for about 3 to about 5 hours.

16. A production method according to claim 13, wherein said reacting is at a temperature ranging from 20 to 30° C. for about 3 to about 5 hours.